United States Patent [19]
Lueddecke et al.

[11] Patent Number: 4,844,934
[45] Date of Patent: Jul. 4, 1989

[54] PREPARATION OF FINELY DIVIDED, WATER-DISPERSABLE CAROTENOID FORMULATIONS

[75] Inventors: Erik Lueddecke, Mutterstadt; Dieter Horn, Heidelberg, both of Fed. Rep. of Germany

[73] Assignee: BASF Aktiengesellschaft, Ludwigshafen, Fed. Rep. of Germany

[21] Appl. No.: 28,545

[22] Filed: Mar. 20, 1987

[30] Foreign Application Priority Data

Mar. 26, 1986 [DE] Fed. Rep. of Germany ....... 3610191

[51] Int. Cl.$^4$ ...................... A23L 1/275; A23L 1/303; B01J 13/00
[52] U.S. Cl. ..................................... 426/540; 426/96; 426/98; 252/309; 252/314; 252/363.5; 514/772
[58] Field of Search ............... 426/540, 96, 98; 8/506; 514/772; 252/309, 314, 363.5

[56] References Cited

U.S. PATENT DOCUMENTS

| | | | |
|---|---|---|---|
| 2,861,891 | 11/1958 | Bauernfeind et al. | 426/540 |
| 3,110,598 | 11/1963 | Müller et al. | 426/540 |
| 3,125,451 | 3/1964 | Wingerd et al. | 426/540 |
| 3,206,316 | 9/1965 | Klaui | 426/540 |
| 3,316,101 | 4/1967 | Borenstein et al. | 426/540 |
| 3,655,406 | 4/1972 | Klaui | 426/540 |
| 3,998,753 | 12/1976 | Antoshkiw et al. | 426/540 |
| 4,522,743 | 6/1985 | Horn et al. | 426/540 |

FOREIGN PATENT DOCUMENTS 50-75215  6/1975  Japan .................................. 426/540

OTHER PUBLICATIONS

H. Klaui, Wiss. Veroffentl. Deutsch. Ges. f. Ernahrung 9, (1963), p. 396.

Primary Examiner—Wilbur Bascomb
Attorney, Agent, or Firm—Keil & Weinkauf

[57] ABSTRACT

Water-disperable carotenoid formulations are prepared by dissolving the carotenoid in a carrier oil at elevated temperatures until saturation is achieved, rapidly emulsifying the solution with an aqueous protective colloid and then removing the water, by a process in which the protective colloid used is a mixture of an ester of a long-chain fatty acid with ascorbic acid and a starch product which is soluble in cold water.

The produce can be used for coloring foods and is stable to creaming.

9 Claims, No Drawings

PREPARATION OF FINELY DIVIDED, WATER-DISPERSABLE CAROTENOID FORMULATIONS

The present invention relates to a process for the preparation of finely divided carotenoid emulsions having high color strength, and of carotenoid-containing dry powders which are obtained from these emulsions and are dispersable in cold water, using a mixture of an ester of a long-chain fatty acid with ascorbic acid and, as a colloid, a starch product which is soluble in cold water.

The colors of a large number of plants and animals are determined by substances belonging to the carotenoid group. These are compounds which have intense yellow to red colors. In addition to the naturally occurring carotenoids, other known carotenoids are those which can only be synthesized. The most important members of the two classes are $\beta$-carotene, canthaxanthin, citranaxanthin, $\beta$-apo-8'-carotenal and esters of $\beta$-apo-8'-carotenic acid. Because they are not harmful to health and in some cases even have a health-promoting provitamin A action, these compounds are increasingly being used as colorants or additives for food, drugs, cosmetics and animal feeds.

While oily or fatty systems can be fairly readily colored with the pure crystalline substances, aqueous systems are virtually impossible to color with the substances. Furthermore, pure carotenoids mixed with food or animal feed are very poorly utilized by the human or animal organism. The reason for this is the complete insolubility of most carotenoids in water. The carotenoids have only very limited solubility even in organic solvents such as alcohols and alkanes.

U.S. Pat. No. 2,861,891 has therefore described a process for the preparation of water-dispersable carotene formulations. In this process, the carotenoid, eg. $\beta$-carotene as one of the most important members of this group, is dissolved in a vegetable oil at elevated temperatures, this oil solution is emulsified in an aqueous protective colloid system and the resulting emulsion is converted to a dry powder by removal of water.

If the dry powder is redispersed in warm water, a cloudy, orange yellow emulsion is formed again. This can be used, for example, for coloring foods. Important performance characteristics of these coloring formulations are solubility, hue, color strength, turbidity and stability in the medium used. Good solubility in cold water, an intense yellow hue, a low level of turbidity and high stability even in acidic solution ($2 < \text{pH} < 4$) are advantageous for many users.

In the prior art, some of these properties are obtained by using gum arabic as a protective colloid in the aqueous phase. However, the use of gum arabic in a food additive has recently presented very great problems since the quality varies very greatly and moreover the microbiological status of this natural product, which accumulates in the human body, does not meet the requirements of quality-conscious food producers.

According to H. Kläui in Wiss. Veroffentl. Deutsch. Ges. f. Ernährung 9, (1963) p. 396, dextrin too has been mentioned as a protective colloid. However, this publication points out that the products obtained are still not completely satisfactory owing to their tendency to cream in citrus beverages.

It is an object of the present invention to provide a protective colloid which does not have the stated disadvantages and imparts all the required properties to the carotene formulation.

We have found that this object is achieved, according to the invention, by a process for the preparation of a water-dispersable carotenoid formulation by dissolving the carotenoid in a carrier oil at elevated temperatures until saturation is achieved, rapidly emulsifying the solution with an aqueous protective colloid and then removing the water, wherein the protective colloid used is a mixture of an ester of a long-chain fatty acid with ascorbic acid and a starch product which is soluble in cold water.

This process permits the preparation of a gum arabic-free carotenoid formulation which has very good disperability in cold water in the dry state, an intense yellow hue coupled with high specific color strength and a low level of turbidity in the dispersed state, and high stability in both the dry state and the dispersed state.

The following specific mixtures are advantageously used:

1. An mixture of a starch product, which is soluble in cold water, and ascorbyl palmitate, with or without the addition of lecithin and sugar in water is used as the protective colloid solution. Of the large number of commercially available starch products which are soluble in cold water, only certain products have sufficient emulsifying activity. The choice can be made on the basis of the size of the emulsion droplets obtained in an emulsion prepared and described in Example 1 (with variation of the dextrin). The droplet size, determined by photon correlation spectroscopy, must not fall below a mean diameter of 0.5 $\mu$m. The amount of dextrin is from 5 to 90, preferably from 10 to 50, particularly preferably from 15 to 30%, by weight, based on the end product. Particularly suitable starch products which are soluble in cold water are dextrin and modified starch, eg. starch octenyl succinate.

Dextrin is a partially hydrolyzed starch which is obtained, either by means of heat alone or heat in the presence of an acid, from various starches (corn starch, potato starch, wheat starch, rice starch etc.), as described in, for example, "Food Chemical Codex", third edition 1981, National Academy Press, page 96, or "Starch: Chemistry and Technology", Academic Press, Inc. (1984), second edition, which are herein incorporated by reference. The degree of hydrolysis is generally stated as dextrose equivalent (DE). It is a measure of the amount of reducing sugar, calculated as D-glucose and based on dry weight. The DE value is the reciprocal of the degree of polymerization. Unhydrolyzed starch has a DE value of virtually 0, while, in conformity with the definition, C-glucose has a DE value of 100.

Suitable dextrin has, for example, a DE value of less than 20, preferably from 1 to 8.

The ratio of the said cold water-soluble starch product to the ester of a long-chain fatty acid with ascorbic acid is in general from 100:1 to 1:1, preferably from 50:1 to 10:1.

The ester of a long-chain fatty acid, which as a rule is a fatty acid of, for example, 18 carbon atoms, with ascorbic acid, in particular ascorbyl palmitate (AP), has a double function in this protective colloid solution. On the one hand, it acts as an emulsifier, ie. the emulsion becomes stable to creaming only after the addition of the AP and the achievable drop size is reduced as desired. This action was surprising since the literature attributes the emulsifying action of the AP only to the corresponding sodium salt (German Pat. No. 1,190,314); in the present protective colloid solution, however, the pH is in the acidic range, so that AP is not present in the form of the salt. Secondly, it acts as an antioxidant, as disclosed in the literature. The concentration is from 0.5 to 4, preferably 2, % by weight, based on the ready-prepared dry powder.

The addition of lecithin further increases the stability of the carotenoid to heat and light; the concentration is from 0 to 2, preferably 1, % by weight. Sugar in the formulation serves as a platicizer and increases the mechanical and thermal stability of the end product. Glucose syrup is preferably used; the amount depends on the amount of the starch product which is soluble in cold water, and is from 0 to 85%, preferably 65%.

The amount of water is chosen so that a low viscosity emulsion results; viscosity should be from 5 to 50, preferably 10, mPas at 60° C.

The carotenoid is dispersed in vegetable oil and finely milled, and tocopherol is introduced as an additional antioxidant. Examples of suitable vegetable oils are orange peel oil, soya bean oil, cotton seed oil and peanut oil. The concentration of the carotenoid in the oil should be from 10 to 30, preferably 20%, by weight. The carotenoid should be milled so that the resulting particle size distribution substantially excludes crystals >10 μm. This ensures uniform solution kinetics. The tocopherol used may be either natural or synthetic tocopherol (d-l-α-tocopherol). The ratio of carotenoid to tocopherol in the mixture is from 3:1 to 1:3, preferably 1:1. The resulting dispersion is referred to below as the oil phase.

The oil phase is then heated for a short time until the carotenoid has completely dissolved in th carrier oil. The resulting carotene solution is passed into the aqueous protective colloid solution and emulsified. The amount of oil phase is such that the desired carotenoid concentration is obtained in the end product. This is from 0.1 to 2%, a concentration of 1% being optimum.

The minimum drop size obtainable by these measures is dependent on the type of emulsifying apparatus, the formulation and the duration of emulsification. If a dispersing apparatus functioning on the principle of the rotor-stator is used and the preferred ratio of starting materials is chosen, a mean particle size of 0.3 μm ±50% is obtained. This is unusually low for an O/W emulsion and is very advantageous with regard to the end product since both color strength and hue and turbidity are shifted in the stated advantageous direction as th droplets become smaller. The particle size is measured by photon correlation spectroscopy, as for the choice of the dextrins.

3. The resulting emulsion has a long shelf life and can either be used directly for coloring foods, if necessary with the addition of preservatives, or be subjected to a known process for removing water under mild conditions, for example by spray drying, and then converted to a dry powder which has the special properties stated at the outset.

The properties, described at the outset, of the carotenoid formulations prepared by this process, ie. good dispersability in cold water, high specific color strength, low turbidity and, in the case of β-carotene, an intense yellow hue, cannot be achieved in this combination using other formulating methods known from the literature. Although the dispersion containing very fine carotenoid particles and having a correspondingly low turbidity can be prepared, for example as described in German Laid-Open Application DOS No. 2,534,091, by dissolving the carotenoid in a volatile organic solvent, emulsifying this solution in an aqueous carrier system and then removing the organic solvent by evaporation, the oil droplets which contain β-carotene in solution in molecular form and are responsible for the special coloration according to the process described are not present after this process. Furthermore, the use of an emulsifier which is not acceptable under food law, as required by German Laid-Open Application DOS No. 2,534,091, presents problems. The process described in European Pat. No. 65,193 also gives discrete carotenoid particles which have a coloring activity which differs from that of the dissolved carotene.

EXAMPLE 1

375 ml of water, 75 g of dextrin (Nadex ®4772 from National Startch), 253 g of glucose syrup (Glucodex ®127 from Maizena), 6 g of ascorbyl palmitate and 1.65 g of lecithin (Emulfluid ®E from Lucas-Mayer) are initially taken in a 1 l beaker, mixed thoroughly to give a homogeneous mixture and heated to 60° C. Independently of this, 3 g of DL-α-tocopherol and 18 g of β-carotene dispersion (20% strength dispersion in peanut oil) are thoroughly mixed in a 250 ml four-necked round-bottomed flask. The round-bottomed flask is warmed in an oil bath heated to 180° C., until the β-carotene has completely dissolved. The oil solution is then passed into the aqueous phase, while stirring with a homogenizer (Ultra Turrax T 45 from Janke and Kunkel) at 10,000 rpm. After an emulsification time of 15 minutes, a yellowish orange emulsion having an oil droplet size of about 0.3 μm, high color strength and a long shelf life is obtained. Removal of water by spray drying gives a free-flowing powder which is disperable in cold water and contains 1.1% of β-carotene.

COMPARATIVE EXAMPLE 1

375 ml of water, 75g of dextrin (Nadex ®4722 from National Starch), 253 g of glucose syrup (Glucodex ®127 from Maizena) and 1.65 g of lecithin (Emulfluid ®E from Lucas-Mayer) are initially taken in a 1 l beaker, mixed thoroughly to give a homogeneous mixture and heated to 60° C. Independently of this, 3 g of DL-α-tocopherol and 18 g of β-carotene dispersion (20% strength dispersion in peanut oil) are thoroughly mixed in a 250 ml four-necked round-bottomed flask. The round-bottomed flask is warmed in an oil bath heated to 180° C., until the β-carotene has completely dissolved. The oil solution is then passed into the aqueous phase, while stirring with a homogenizer (Ultra Turrax T 45 from Janke and Knukel) at 10,000 rpm. After an emulsification time of 15 minutes, a cloudy, orange emulsion which exhibits slight creaming on storage at 60° C. for 8 hours is obtained. The droplet size is 0.6–0.7 μm, and the size distribution is very broad. The hydrosol prepared by redissolving the dry powder obtained from the emulsion is likewise cloudy, is slightly reddish and has a specific color strength about 30% lower than that of the hydrosol obtained as described in Example 1.

EXAMPLE 2

375 ml of water, 75 g of starch octenyl succinate (capsules from National Starch), 253 g of glucose syrup (Glucodex ®127 from Maizena), 6 g of ascorbyl palmitate and 1.65 g of lecithin (Emulfluid ®E from Lucas-Mayer) are initially taken in a 1 l beaker mixed thoroughly to give homogeneous mixture and heated to 60° C. Independently of this, 3 g of DL-α-tocopherol and 18 g of β-carotene dispersion (20% strength dispersion in peanut oil) are thoroughly mixed in a 250 ml four-necked round-bottomed flask. The round-bottomed flask is warmed in an oil bath heated to 180° C., until the β-carotene has completely dissolved. The oil solution is then passed into the aqueous phase, while stirring with a homogenizer (Ultra Turrax T 45 from Janke and Kunkel) at 10,000 rpm. After an emulsification time of 15 minutes, a very fine, yellowish orange emulsion having high color strength and having an oil droplet size of about 0.25 μm is obtained.

COMPARATIVE EXAMPLE 2

375 ml of water, 75 g of starch octenyl succinate (capsules from National Starch), 253 g of glucose syrp (Glucodex ®127 from Maizena) and 1.65 g of lecithin (Emulfluid ®E from Lucas-Mayer) are initially taken in a 1 l beaker, mixed thoroughly to give a homogeneous mixture and heated to 60° C. Independently of this, 3 g of DL-α-TOCOPHEROL AND 18 G OF β-carotene dispersion (20% strength dispersion in peanut oil) are thoroughly mixed in a 250 ml four-necked round-bottomed flask. The round-bottomed flask is warmed in an oil bath heated to 180° C., until the β-carotene has completely dissolved. The oil solution is then passed into the aqueous phase, while stirring with a homogenizer (Ultra Turrax T 45 from Janke and Kunkel) at 10,000 rpm. After an emulsification time of 15 minutes, a cloudy, orange emulsion which exhibits creaming on storage at room temperature for 15 hours is obtained. Droplet size is 0.5 μm, and the size distribution is very broad.

We claim:

1. A process for the preparation of a water-dispersible carotenoid formulation by dissolving the carotenoid in a carrier oil at elevated temperatures until saturation is achieved to form a carotenoid solution, rapidly emulsifying the carotenoid solution with an aqueous protective colloid and then removing the water, wherein the protective colloid is a solution having a pH in the acidic range and consists essentially of a combination of a long-chain fatty acid ester of ascorbic acid and a cold water soluble starch product.

2. A process for the preparation of a water-dispersible carotenoid formulation by dissolving the carotenoid in a carrier oil at elevated temperature until saturation is achieved to form a carotenoid solution, rapidly emulsifying the carotenoid solution with an aqueous protective colloid and then removing the water, wherein the protective colloid is a solution having a pH in the acidic range and consists essentially of a combination of (A) an ascorbyl ester of a fatty acid of 18 carbon atoms and (B) a cold water soluble starch product selected from the group consisting of chemically modified starch and dextrin with a dextrose equivalent of less than 20, the weight ratio of (A) to (B) being from 1:100 to 1:1.

3. The process of claim 1, wherein ascorbyl palmitate is the long-chain fatty acid ester of ascorbic acid.

4. The process of claim 1, wherein dextrin or chemically modified starch is the cold water soluble starch product.

5. The process of claim 6, wherein the starch product is starch octenyl succinate.

6. The process of claim 1, wherein the starch product is dextrin.

7. The process of claim 3, wherein lecithin and tocopherol are also added to the carotenoid solution.

8. The process of claim 3, wherein lecithin and tocopherol are also added to the carotenoid solution, wherein the carotenoid is β-carotene and wherein the starch product is dextrin.

9. The process of claim 3, wherein lecithin and tocopherol are also added to the carotenoid solution, wherein the carotenoid is β-carotene and wherein the starch product is starch octenyl succinate.

* * * * *